United States Patent [19]
Boulikas

[11] Patent Number: 6,030,956
[45] Date of Patent: *Feb. 29, 2000

[54] COMBINATION GENE THERAPY FOR HUMAN CANCERS

[76] Inventor: Teni Boulikas, 249 Matadero Ave., Palo Alto, Calif. 94306

[ * ] Notice: This patent issued on a continued prosecution application filed under 37 CFR 1.53(d), and is subject to the twenty year patent term provisions of 35 U.S.C. 154(a)(2).

[21] Appl. No.: 08/956,994

[22] Filed: Oct. 23, 1997

Related U.S. Application Data

[60] Provisional application No. 60/029,761, Oct. 24, 1996.

[51] Int. Cl.⁷ ............... C12N 15/00; A01N 43/04; C07H 21/04; B32B 5/16
[52] U.S. Cl. ............... 514/44; 536/23.2; 536/23.5; 536/24.1; 428/402.2; 435/320.1
[58] Field of Search ............... 514/44; 424/93.2; 536/23.2, 23.5, 24.1; 428/402.2; 435/320.1

[56] References Cited

PUBLICATIONS

Kwong et al. Cancer Gene Therapy 3(5) 339–44, Sep. 1996.
Mujoo et al. Oncogene 12(8) 1617–23, Apr. 1996.
Roth et al. Nature Medicine 2(9) 985–91, Sep. 1996.
Mastrangelo et al. Seminars in Oncology, vol. 23 (1) 4–21, Feb. 1996.
Orkin et al. Report and recommedation of the panel to assess the NIH investment in research on gene therapy, Dec. 1995.

*Primary Examiner*—Bruce R Campbell
*Assistant Examiner*—Shin-Lin Chen
*Attorney, Agent, or Firm*—Judy M. Mohr; Peter J. Dehlinger; Dehlinger & Associates

[57] ABSTRACT

A method of treating cancer in a subject, by administering to the subject a combination of genes including wt p53, Pax5 and HSV-tk genes is disclosed. The method may involve subsequently treating the subject with ganciclovir.

4 Claims, No Drawings

COMBINATION GENE THERAPY FOR HUMAN CANCERS

This application claims priority under 37 CFR §119(e) to Provisional Application Ser. No. 60/029,761 filed Oct. 24, 1996, which is incorporated herein by reference in its entirety.

FIELD OF THE INVENTION

The present invention relates to the use of three different genes, p53, Pax5, and HSV-tk, to kill cancer cells in a variety of human malignancies.

REFERENCES

Anderson, W. F., *Science* 256:808–813 (1992).
Austin, E. A., and Huber, B. H., *Mol. Pharmacol.* 43:380–387 (1993).
Bacchetti, S., and Graham, F. L., *Int. J. Oncol.* 3:781–788 (1993).
Bakalkin, G., et al., *Nucleic Acids Res.* 23:362–369 (1995).
Barak, Y., et al., *EMBO J.* 12:461–468 (1993).
Bargonetti, J., et al., *Cell* 65:1083–1091 (1991).
Borrelli, E., et al., *Proc. Natl. Acad. Sci. USA* 85:7572–7576 (1988).
Boulikas, T., *Crit. Rev. Euk. Gene Exp.* 4:117–321 (1994a).
Boulikas, T., *J. Cell Biochem.* 55:513–529 (1994b).
Boulikas, T., *Int. Rev. Cytol.* 162A:279–388 (1995).
Boulikas, T., *Anticancer Res.* 17:1471–1506 (1996e).
Boulikas, T., and Hu, J., "New vectors for high level expression of the luciferase gene in mammalian cells," *Nucleic Acids Res.*, (1997).
Boulikas, T., and Martin, F., "Agarose gel electrophoresis to determine plasmid-cationic liposome interactions," *Nucleic Acids Res.*, (1996a).
Boulikas, T., and Martin, F., "Histones, protamine, and polylysine but not poly (E:K) enhance transfection efficiency," Submitted, (1996b).
Boulikas, T., et al., "The 5' regulatory region of the human choline acetyltransferase gene is anchored to the nuclear matrix and has origin of replication activity," *Science*, (1996a).
Boulikas, T., et al., "DNA condensation with spermine increases transfection efficiency and cationic liposome-mediated plasmid uptake," *Biochemistry*, (1996b).
Chen, C.-Y., et al., *Proc. Natl. Acad. Sci. USA* 91:2684–3688 (1994).
Chen, Y., et al., *Oncogene* 6:1799–1805 (1991).
Chi, S. G., et al., *J. Natl. Cancer Inst.* 86:926–933 (1994).
Chin, K.-V., et al., *Science* 255:459–462 (1992).
Culver, K. W., et al., *Science* 256:1550–1552 (1992).
Dameron, K. M., et al., *Science* 265:1582–1584 (1994).
Deb, S. P., et al., *J. Virol.* 66:6164–6170 (1992).
Deb, S. P., et al., *Oncogene* 9:1341–1349 (1994).
Deffie, A., et al., *Mol. Cell. Biol.* 13:3415–3423 (1993).
Deppert, W., *Sem. Cancer Biol.* 5:187–202 (1994).
Diller, L., et al., *Mol. Cell. Biol.* 10:5772–5781 (1990).
Dimaio, J. M., et al., *Surgery* 116:205–213 (1994).
Dinjens, W. N., et al., *Int. J. Cancer* 56:630–633 (1994).
Dittmer, D., et al., *Nature Genet.* 4:42–45 (1993).
Donehower, L. A., et al., *Nature* 356:215–221 (1992).
Dubey, D. D., et al., *Mol. Cell. Biol.* 11:5346–5355 (1991).
Dutta, A., et al., *Nature* 365:79–82 (1993).
Eastham, J. A., et al., *Hum. Gene Ther.* 7:515–523 (1996).
Eastham, J. A., et al., *Cancer Res.* 55:5151–5155 (1995).
El-Deiry, W. S., et al., *Cell* 75:817–825 (1993).
Farmer, G., et al., *Nature* 358:83–86 (1992).
Field, A. K., et al., *Proc. Natl. Acad. Sci. USA* 80:4139–4143 (1983).
Friedman, P. N., et al., *Proc. Natl. Acad. Sci. USA* 87:9275–9279 (1990).
Fujiwara, T., et al., *J. Natl. Cancer Inst.* 86:1458–1462 (1994).
Gassmann, M., et al., *Proc. Natl. Acad. Sci. USA* 92:1292–1296 (1995).
Harvey, M., et al., *Nature Genet.* 5:225–229 (1993).
Hirt, B., *J. Mol. Biol.* 26:365–369 (1967).
Hollstein, M., et al., *Science* 253:49–53 (1991).
Huber, B. E., et al., *Cancer Res.* 53:4619–4626 (1993).
Huber, B. E., et al., *Proc. Natl. Acad. Sci. USA* 88:8039–8043 (1991).
Hupp, T. R., et al., *Cell* 71:875–886 (1992).
Isaacs, W. B., et al., *Semin. Oncol.* 21:514–521 (1994).
Isaacs, W. B., et al., *Cancer Res.* 51:4716–4720 (1991).
Jayaraman, L., and Prives, C., *Cell* 81:1021–1029 (1995).
Kastan, M. B., et al., *Cell* 71:587–597 (1992).
Kato, K., et al., *J. Biol. Chem.* 266:3361–3364 (1991).
Kern, S. E., et al., *Science* 252:1708–1711 (1991).
Kern, S. E., et al., *Science* 256:827–830 (1992).
Kimura, H., et al., *Hum. Gene Ther.* 7:799–808 (1996).
Ko, S.-C., et al., *Hum. Gene Ther.* 7:1683–1691 (1996).
Lane, D. P. and Crawford, L. V., *Nature* 278:261–263 (1979).
Lasic, D. D., and Martin, F. J., (Eds.) in *STEALTH LIPOSOMES* CRC Press Boca Raton, Fla., PP 1–289 (1995).
Lasic, D. D., and Templeton, N. S., *Adv. Drug Del. Rev.* (1996).
Lee, R. J., and Low, P. S., *Biochim. Biophys. Acta* 1233:134–144 (1995).
Lee, S., et al., *Cell* 81:1013–1020 (1995).
Lesoon-Wood, L. A., et al., *Hum. Gene Ther.* 6:395–405 (1995).
Levine, A. J., *Ann. Rev. Biochem.* 62:623–651 (1993).
Lew, D., et al., *Hum. Gene Ther.* 6:553–564 (1995).
Li, R., and Botchan, M. R., *Cell* 73:1207–1221 (1993).
Li, R., et al., *Nature* 371:534–537 (1994).
Linzer, D. P. and Levine, A. J., *Cell* 17:43–52 (1979).
Lu, X., and Lane, D. P., *Cell* 75:765–778 (1993).
Miller, S. D., et al., *Mol. Cell. Biol.* 15:6554-6560 (1995).
Miyashita, T., et al., *Oncogene* 9:1799–1805 (1994a).
Miyashita, T., et al., *Cancer Res.* 54:3131–3135 (1994b).
Miyashita, T., and Reed, J. C., *Cell* 80:293–299 (1995).
Momand, J., et al., *Cell* 69:1237–1245 (1992).
Moolten, F. L., *Cancer Res.* 46:5276–5281 (1986).
Moolten, F. L., and Wells, J. M., *J. Natl. Cancer Inst.* 82:297–300 (1990).
Mullen, C. A., et al., *Proc. Natl. Acad. Sci. USA* 89:33–37 (1992).
Mummenbrauer, T., et al., *Cell* 85:1089–1099 (1996).
Nelson, W. G., and Kastan, M. B., *Mol. Cell. Biol.* 14:1815–1823 (1994).
Okamoto, K., and Beach, D., *EMBO J.* 13:4816–4822 (1994).
Oliner, J. D., et al., *Nature* 358:80–83 (1992).
Osaki, T., et al., *Cancer Res.* 54:5258–5261 (1994).
Papathanasiou, M. A., et al., *Mol. Cell Biol.* 11:1009–1016 (1991).
Perry, M. E., et al., *Proc. Natl. Acad. Sci. USA* 90:11623–11627 (1993).
Prives, C., *Cell* 78:543–546 (1994).
Prives, C., and Manfredi, J. J., *Genes Dev.* 7:529–534 (1993).
Richards, C. A., et al., *Hum. Gene Ther.* 6:881–893 (1995).
Roth, J. A., *Hum. Gene Ther.* 7:1013–1030 (1996).

Roth, J. A., et al., *Nature Med.* 2:985–991 (1996).
Russev, G., and Boulikas, T., *Eur. J. Biochem.* 204:267–272 (1992).
Shivakumar, C. V., et al., *Mol. Cell. Biol.* 15:6785–6793 (1995).
Smith, M. L., et al., *Science* 266:1376–1380 (1994).
Stuart, E., et al., *EMBO J.* 14:5638–5645 (1995).
Su, H., et al., *Hum. Gene Ther.* 7:463–470 (1996).
Thierry, A. R., et al., *Proc. Natl. Acad. Sci. USA* 92:9742–9746 (1995).
Tsutsumi-Ishi, Y., et al., *Cell Growth Differ.* 6:1–8 (1995).
van den Heuvel, S. J. L., et al., *EMBO J.* 9:2621–2629 (1990).
Voeller, H. J., et al., *J. Urol.* 151:492–495 (1994).
Vogelstein, B., *Nature* 348:681–682 (1990).
Vogelstein, B., and Kinzler, K., *Cell* 70:523–526 (1992).
Waga, S., et al., *Nature* 369:574–578 (1994).
Wang, E. H., et al., *Cell* 57:379–392 (1989).
Westerman, K. A., and Leboulch, P., *Proc. Natl. Acad. Sci. USA* 93:8971–8976 (1996).
Wilcock, D., and Lane, D. P., *Nature* 349:429–431 (1991).
Wills, K. N., et al., *Human Gene Ther.* 5:1079–1088 (1994).
Yang, C., et al., *Cancer Res.* 55:4210–4213 (1995).
Yew, P. R., and Berk, A. J., *Nature* 357:82–85 (1992).
Zambetti, G. P., and Levine, A. J., *FASEB J.* 7:855–865 (1993).
Zambetti, G. P., et al., *Genes Dev.* 6:1143–1152 (1992).
Zastawny, R. L., et al., *Oncogene* 8:1529–1535 (1993).

BACKGROUND OF THE INVENTION

Although the important role of p53 and mutations in the p53 gene in cancer etiology has been established and gene transfer has advanced enormously in the last ten years only a limited number of studies have addressed the transfer of the p53 gene into malignant cultured cells to render them non-tumorigenic after injection into nude mice; even a smaller number of studies have used transfer of the p53 gene in animal models (for example Ko, et al., 1996). A clinical protocol at M. D. Anderson Cancer Center (Houston, Tex.) proposed the transfer of wt p53 gene with and without cisplatin in non-small cell lung cancer patients shown to have mutations in the p53 gene using adenovirus5-CMV-p53 construct (Roth, 1996) and p53 adenovirus driven by the b-actin promoter (Roth, et al., 1996).

Cells from over 85% of human malignancies are associated with mutations in the p53 tumor suppressor gene. The wild-type (normal, non mutated) p53 gene plays a pivotal role in arresting the cell cycle and the proliferation of cells after severe damage to the DNA; the mechanism is thought to involve the upregulation of the p21/WAF-1/Cip-1 gene (see below) whose product can interact with PCNA (proliferating cell nuclear antigen), an accessory molecule to DNA polymerase d causing inhibition in DNA replication but also by inhibition of CDK (cyclin-dependent kinase) by p21; CDK is responsible for phosphorylating RB at a strategic site causing transversion of the cell cycle through the G1/S checkpoint (Boulikas, 1997).

Furthermore, p53 upregulates the death-inducing gene BAX and down-regulates the Bcl-2 gene promoting cells to enter the apoptotic pathway; mutant p53, such as that found in the majority of human tumors, has lost the capacity of transactivating the p21, BAX and other genes; indeed, the most frequent inactivating mutations occur at the DNA-binding domain of p53 at strategic amino acid sites that contact DNA.

Although the cause versus effect of p53 mutations on human malignancies is not clear for many cases, overexpression of an exogenous wild-type (wt) p53 gene followed by suppression of the endogenous mutated gene of p53 that can have an antagonizing effect to wt p53, is an approach found to suppress tumorigenicity of cells in culture and is proposed here as a method for cancer treatment.

Central to this patent is our demonstrated ability to specifically target tumor cells in culture using the luciferase reporter gene, as well therapeutically important genes, in supercoiled plasmids under control of tissue-specific and tumor specific control elements including but not limited to matrix-attached regions (MARs) (Boulikas, et al., in preparation).

MARs are claimed as largely responsible for mediating the effects of p53 on cell cycle arrest both in the sense that the regulatory regions of p53 targets (p21, BAX, PCNA regulatory regions) might be associated with the nuclear matrix as well as by the established property of MARs to be enriched in triplex-, cruciform- and other unusual DNA structures including stretches of cruciforms with insertion deletion mismatches. We claim that wt and mutant (mu) p53 interact differently with MAR DNA.

I. p53 as a Tumor Suppressor Protein

Alterations in the p53 tumor suppressor gene appear to be involved, directly or indirectly, in the majority of human malignancies (Vogelstein, 1990). Both alleles of p53 need to be mutated or altered for transformation. Introduction of a null mutation by homologous recombination in murine embryonic stem cells gave mice which appeared normal but were susceptible to a variety of neoplasms by 6 months of age (Donehower, et al., 1992; Harvey, et al., 1993).

The tumor suppressive activity of p53 seems to involve at least four independent pathways: (i) upregulation of specific genes most important of which appears to be p21; p21 up-regulation inhibits the activity of cyclin-dependent kinases (CDKs) leading to inability to phosphorylate RB and to release E2F from its complex with RB; released E2F upregulates genes whose products are needed for DNA synthesis (reviewed by Boulikas, 1995e). p21 induction also leads to p21 association with proliferating cell nuclear antigen (PCNA) leading to the inactivation of the PCNA function as an auxiliary factor for DNA polymerase d and to arrest in DNA synthesis in S phase; (ii) induction of the death-promoting bax gene and down-regulation of bcl-2 gene as a mechanism which eliminates oncogenic virus-infected and transformed cells and as an important mediator of apoptosis during embryogenesis and in B cell maturation; (iii) direct interaction of p53 with origins or replication preventing firing and initiation of DNA replication; (iv) induction of Gadd45 leading to growth arrest; (v) a role of p53 in DNA repair; p53 is believed to patrol the genome for small insertion deletion mismatches (Lee, et al., 1995) or free ends of DNA able to attract RPA, an accessory to DNA polymerases a and d as well as TFIIH at the damaged sites (both TFIIH and RPA have a demonstrated role in DNA repair) and to induce arrest in the cell cycle or apoptosis after DNA damage (see below); (vi) upregulation of the gene of thrombospondin inhibiting which inhibits neovascularization in solid tumors (Dameron, et al., 1994); and (vii) an immune response in solid tumors after local injection of the adenoviral/p53 gene which elicits an immune reaction leading to tumor necrosis (Ko, et al., 1996).

Protein p53 appears to be a transcription factor able to recognize specific regulatory regions in a number of genes via its central DNA-binding domain; the DNA sequence-specific binding of wt p53 is regulated by the C-terminal domain of p53 and is activated by a variety of posttranslational modifications (Hupp, et al., 1992; reviewed by Hupp and Lane, 1994).

Increased levels of p53 up regulate the expression of specific genes including Cip-1/Waf-1/p21 (El-Deiry, et al., 1993), GADD45 (Kastan, et al., 1992), cyclin G (Okamoto and Beach, 1994), and mdm2 (Perry, et al., 1993; Barak, et al., 1993; Momand, et al., 1992) which is induced by UV damage in a p53-dependent pathway (Perry, et al., 1993). Other genes up-regulated by p53 include human PCNA (Shivakumar, et al., 1995), mouse muscle creatine kinase MCK (Zambetti, et al., 1992), EGFR (Deb, et al., 1994), GADD45 (Kastan, et al., 1992), the potent promoter of the death pathway Bax (Miyashita and Reed, 1995), and thrombospondin-1 (Dameron, et al., 1994).

Mdm2 acts as a feedback loop for the biological functions of p53 apparently to moderate the G1/S arrest or apoptosis triggered by p53 following severe damage to DNA. Mdm2 protein associates with p53 causing p53 inactivation by preventing its sequence-specific binding to regulatory targets in DNA (Momand, et al., 1992; Oliner, et al., 1992). Elevated levels of Mdm2 mimic the effect of T antigen, E11 B of adenovirus, E6 of HPV, which also inactivate p53 in a similar manner; overexpression of Mdm2 can block the induction of apoptosis by p53 (Chen, et al., 1994).

Gadd45 is believed to inhibit cell cycle progression; however, the mechanism has not been elucidated (Papathanasiou, et al., 1991).

The PCNA promoter is up-regulated in the presence of moderate amounts of wt p53; however, at higher levels of wt p53 the PCNA promoter is inhibited whereas tumor-derived p53 mutants activate the PCNA promoter (Shivakumar, et al., 1995); it has been suggested that the moderate elevation in wt p53 seen after DNA damage induces PCNA to cope with its DNA repair activities (Shivakumar, et al., 1995); this inhibition in DNA replication but stimulation in repair by p53 might be accomplished by an independent pathway involving induction of p21 (El-Deiry, et al., 1993) which interacts with PCNA protein auxiliary to DNA polymerase d to inhibit the replication but not the repair functions of PCNA (Li, et al., 1994).

The bax gene which induces apoptosis is upregulated by p53 whereas the bcl-2 gene which inhibits apoptosis in B cells is down-regulated by p53 (Miyashita, et al., 1994a, 1994b; Miyashita and Reed, 1995). Initiated cancer cells may lead to tumor development only when a dysfunction in their apoptotic pathway takes place; some of the mechanisms leading to inactivation of the apoptotic pathway in cancer cells may result from an up-regulation in the bcl-2 gene (a Bcl-2 chimeric factor is produced in leukemias as a result of a translocation) or down-regulation of the bax gene. Gene therapy for cancer could involve restoration of the apoptotic pathway in cancer cells leading to their suicidal death; this could be effected by overexpression of the bax gene or in the suppression of the endogenous bcl-2 gene for example using p53 expression vectors).

p53 binding sites have been found at the origin of replication of polyomavirus with an inhibitory effect on virus replication in vitro (Miller, et al., 1995) and at the SV40 ORI (Bargonetti, et al., 1991) as well as in putative cellular origins of replication (Kern, et al., 1991). p53 interacts with replication protein A (RPA) (implicated in DNA replication and in repair; interaction of p53 inhibits the replication functions of RPA (Dutta, et al., 1993) although interaction of p53 with RPA via its acidic domains stimulate BPV-1 DNA replication in vitro (Li and Botchan, 1993). Immunolocalization of p53 (also of RB and host replication proteins) at foci of viral replication in HSV-infected cells (Wilcock and Lane, 1991) provided further evidence for a direct interaction of p53 with proteins (or DNA sequences) at the replication fork. Wild-type p53 suppressed DNA replication in vitro when the p53 binding site $(RGC)_{16}$ from the ribosomal gene cluster was cloned on the late side of the polyomavirus (Py) core origin; when mutated p53-binding sites were used, the inhibition in Py replication was not observed. In addition, RPA (able to interact directly with p53) was unable to relieve the p53-mediated repression in Py replication.

The tumor suppressor p53 has the ability to recognize via its C-terminal domain DNA insertion/deletion mismatches consisting of one or a few extra bases on one strand (Lee, et al., 1995).

p53 binds to strand breaks in DNA (Lu and Lane, 1993; Nelson and Kastan, 1994); electron microscopy studies have shown that the C-terminal domain of p53 binds directly to ends of single-stranded DNA whereas the central domain of p53 binds to more internal segments (Bakalkin, et al., 1995). Short single strands considerably stimulate the sequence-specific binding of p53 to its cognate sites in supercoiled DNA and this recognition also involves the C-terminal domain of p53 (Jayaraman and Prives, 1995); a 29 nt segment of DNA known to arise by two endonuclease cuts during NER in mammalian cells around the lesion could stimulate p53 binding to DNA and might play some physiological function in the subsequent steps of repair (Jayaraman and Prives, 1995).

II. Differences in Biological Functions Between Wild-Type p53 and Tumor-Derived p53 Mutants Tumor-derived mutant forms of p53 have lost their DNA sequence-specific binding capacities. For example the Trp-248 and His-273 mutants of p53 have poor DNA-binding abilities and are unable to activate transcription from constructs containing p53 binding sites (Farmer, et al., 1992).

A. Wild Type

Wild-type (wt) p53 tumor suppressor protein negatively regulates cell growth (Hollstein, et al., 1991; Prives, 1994). Whereas the wild-type p53 acts as a tumor suppressor, several of the mutant forms display oncogenic activities (Levine, 1993; Prives and Manfredi, 1993; Deppert, 1994). Although the wt p53 has been postulated to repress growth by activating genes that repress growth (p21), many of the mutant forms have lost their DNA sequence-specific binding and transcriptional activation capacities (reviewed by Zambetti and Levine, 1993).

According to one model (see Vogelstein and Kinzler, 1992), wt p53 is a positive regulator for the transcription of genes that by themselves are negative regulators of growth control and/or invasion. Indeed, p53 upregulates the genes of p21/CIP1/WAF1(El-Deiry, et al., 1993) and GADD45 (Kastan, et al., 1992) whose products interact with PCNA to inhibit its association with DNA polymerase d thus causing arrest in DNA replication (Waga, et al., 1994; Smith, et al., 1994). This feature of p53 that is central to its ability to suppress neoplastic growth is lost by mutations on p53 that result in loss of its ability to bind to DNA or to interact with other transcription protein factors (see also Farmer, et al., 1992; Kern, et al., 1992).

B. Mutant p53

Mutant p53 can transactivate genes that up-regulate cellular growth (Deb, et al., 1992; Dittmer, et al., 1993) such as PCNA (Shivakumar, et al., 1995), EGFR (Deb, et al., 1994), multiple drug resistance (MDR1) (Chin, et al., 1992; Zastawny, et al., 1993), and human HSP70 in vivo (Tsutsumi-Ishi, et al., 1995). These studies support the idea for an oncogene function of the mutant p53 protein compared with the tumor suppressor function of wt p53; mutation in the p53 gene may, thus, cause gain of new functions such as transforming activation and binding to a distinct class of promoters which are not normally regulated by wt p53 (Zambetti and Levine, 1993; Tsutsumi-Ishi, et al., 1995). At the same time appearance of mutations in the p53 gene result in the loss of function of the wt p53 (Zambetti and Levine, 1993).

The wild-type but not mutant p53 at low levels transactivates the human PCNA promoter in a number of different cell lines; the wild-type p53-response element from the PCNA promoter functions in either orientation when placed on a heterologous synthetic promoter; thus moderate elevation of p53 can induce PCNA, enhancing the nucleotide excision repair functions of PCNA (Shivakumar, et al., 1995). Whereas low levels of wild-type p53 activate the PCNA promoter, higher concentrations of wt p53 inhibit the PCNA promoter, and tumor-derived p53 mutants activate the promoter (Shivakumar, et al., 1995).

SV40 T antigen was unable to act as an initiator of SV40 DNA replication in vitro when complexed with p53 (Wang, et al., 1989); mutant p53 was unable to cause inhibition in the initiating functions of T antigen in vitro (Friedman, et al., 1990).

While the wt p53 is endowed with a 3'-to-5' exonuclease activity, associated with the central DNA-binding domain, and thought to function during repair, replication, and recombination; the $273^{His}$ mutant of p53 has lost the exonuclease activity (Mummenbrauer, et al., 1996).

C. Regulation of the p53 Gene

Very few studies on the regulation of the p53 gene are today available (Deffie, et al., 1993; Stuart, et al., 1995). The p53 gene is activated by the wt p53 but not by the functionally inactive mutant p53 protein; mobility shift assays and methylation interference have pinpointed the +22 to +67 region of the promoter of the p53 gene responsible for up-regulation containing an NF-κB response element and a p53-binding site at 10 of 11 nucleotides (Deffie, et al., 1993); it has been difficult to demonstrate direct binding of p53 to this regulatory region of its own gene and thus p53 may transactivate one or more transcription factors such as PRDII-BF1 (also known as MBP1 and HIVEP1), αA-CRYBP1, and AGIE-BP1 as well as NF-κB that bind the NF-κB response element (Deffie, et al., 1993).

p53 is down-regulated by Pax5 in early steps during embryogenesis is by interacting with a DNA control element within exon 1 of the p53 gene; at later stages of embryogenesis and in bone marrow cells Pax5 expression drops allowing the levels of p53 to rise; increased p53 was proposed to induce either apoptosis or B cell differentiation to plasma cells (Stuart, et al., 1995).

III. Gene Therapy Strategies Based on p53

A. Transfer of the p53 Tumor Suppressor Gene to Cancer Cells

Preclinical studies have shown that both viral and plasmid vectors able to mediate high efficiency delivery and expression of wild-type tumor suppressor p53 gene can cause regression in established human tumors, prevent the growth of human cancer cells in culture, or render malignant cells from human biopsies non-tumorigenic in nude mice. Inhibition in cell proliferation was observed in cell culture and in tumors after induction of p53 expression with adenovirus vectors (Bacchetti and Graham, 1993; Wills, et al., 1994). Intratracheal injection of a recombinant retrovirus containing the wt p53 gene was shown to inhibit the growth of lung tumors in mice nu/nu models inoculated intratracheally with human lung cancer H226Br cells whose p53 gene has a homozygous mutation at codon 254 (Fujiwara, et al., 1994). A number of other studies have shown suppression in tumor cell growth and metastasis after delivery and expression of the wt p53 gene (Diller, et al., 1990; Chen, et al., 1991; Isaacs, et al., 1991). A human clinical trial at M. D. Anderson Cancer Center uses transfer of the wild-type p53 gene in patients suffering with non-small cell lung cancer and shown to have p53 mutations in their tumors using local injection of an Ad5/CMV/p53 recombinant adenovirus at the site of tumor in combination with cisplatin (Roth, et al., 1996).

Delivery of the p53 gene to malignant human breast cancer cells in nude mice using DOTMA:DOPE 1:1 cationic liposomes (400 nmoles liposomes/35 mg DNA) resulted in regression (60% reduction in tumor cell volume) in 8 out of 15 animals treated; animals were receiving one injection every 10 days (Lesoon-Wood, et al., 1995). It was thought that wild-type p53 expression (tumor cells were expressing mutant forms of p53) upregulated p21 gene to inhibit cell growth by inhibition in cyclin-dependent kinases but also via induction of apoptosis preferentially in cancer cells.

B. Delivery of p53 to Prostate Cancer Cells

Prostate cancer cells have a mutated p53 gene: three of five prostate cancer cell lines examined (TSUPr-1, PC3, DU145) and one out of two primary prostate cancer specimens were found to harbor mutations altering the amino acid sequence of the conserved exons 5–8 of the p53 gene; transduction of the p53-defective cell lines with the wt p53 gene using lipofectin showed reduction in tumorigenicity assayed from reduced colony formation and the cells became growth arrested (Isaacs, et al., 1991). Although primary prostate tumors have few mutations in the p53 gene (Voeller, et al., 1994; Isaacs, et al., 1994), specimens from advanced stages of the disease and metastases as well as their cell lines frequently display mutations or deletions at both alleles of the p53 gene (Chi, et al., 1994; Dinjens, et al., 1994).

Introduction of the wt p53 or of the p21 downstream mediator of p53-induced growth suppression into a mouse prostate cancer cell line, deficient for p53, led to an association of p21 with Cdk 2; this interaction was sufficient to downregulate Cdk 2 by 65% (Eastham, et al., 1995). The p21 gene, driven by CMV promoter into an Adenovirus 5 vector, was more effective than the AD5CMV-p53 vector, under control of the same elements as p21, in reducing tumor volume in syngeneic male mice with established s.c. prostate tumors. Tumors were induced by injection of 2 million cells in each animal. These studies suggest that p21 expression might have more potent growth suppressive effect than p53.

Infection of the androgen-independent human prostate Tsu-pr1 cell line lacking functional p53 alleles with recombinant adenovirus vectors (replication-deficient) carrying the p53 gene under control of the CMV promoter resulted in expression of p53 and induced striking morphological changes: the cells were detached from the substratum, condensed, and exhibited breakdown of the nuclear DNA into nucleosome-size fragments characteristic of apoptosis; whereas control cells were able to elicit tumors in nude mice, the AdCMV/p53-infected cells failed to form tumors (Yang, et al., 1995).

Endocrine therapy is ineffective once the prostate cancer becomes androgen-independent; these cancers remain unresponsive to conventional chemotherapy. Androgen-independent and metastatic prostate cancers were established in athymic male mice by co-inoculation with the LNCaP human prostate cancer cell line and the MS human bone stromal cell line; these tumors became necrotic and were successfully eradicated by intratum oral injection of a recombinant p53/adenovirus; the p53 gene was driven by the CMV promoter and the SV40 poly(A) signal placed in the E1 region of Ad5 (Ko, et al., 1996). It was suggested that in addition to the tumor suppressor, apoptotic, and antiangiogenesis function of p53, tumor necrosis was induced by a bystander effect or a general immune response which attracted immune cells to cause tumor cell killing (Ko, et al., 1996).

However, a significant factor to be considered in these approaches is the competition of the wt p53 functions by the endogenous mu p53 expressed in tumor cells; optimal results will be expected if the endogenous mu p53 gene is inhibited with the simultaneous overexpression of the wt p53 gene.

As mutated forms of the p53 tumor suppressor gene are the most frequent in human tumors, down-regulation of the mutated endogenous p53 gene in prostate cancer cells and the simultaneous transfer and expression of a wild-type p53 gene able to undertake the tumor suppressor functions is expected to be of therapeutic value inducing apoptotic death to the prostate cancer cells.

C. Cancer Treatment by Transduction of Suicidal HSV-tk Gene Using Liposomes Followed by Treatment with Ganciclovir The cells in a solid tumor are of different pheno- and geno-types; such differences among cells in the same tumor may include differences in ploidy, rearrangements, translocations, expression of oncogenes or tumor suppressor genes, and spectra of mutations among the various genes. It might therefore be an advantage simply to develop strategies for killing tumor cells rather than correct defective genes that led to the cancer phenotype; a package of additional mutations and/or changes may have accumulated in these cells.

A rather successful gene transfer approach results in the direct suppression of tumor growth by cytotoxic gene therapy. Cancer cells can be induced to be conditionally sensitive to the antiviral drug ganciclovir after their transduction with the thymidine kinase (tk) gene from the herpes simplex virus (HSV); ganciclovir is the 9-{[2-hydroxy-1-(hydroxymethyl)-ethoxy]methyl}guanine (Field, et al., 1983); it is converted by HSV-tk into its monophosphate form which is then converted into its triphosphate form by cellular enzymes and is then incorporated into the DNA of replicating mammalian cells leading to inhibition in DNA replication and cell death (Moolten, 1986; Borrelli, et al., 1988; Moolten and Wells, 1990).

It is only viral TK, not the mammalian enzyme, that can use efficiently ganciclovir as a substrate and this drug has been synthesized to selectively inhibit herpes virus replication (Field, et al., 1983); indeed, the mammalian TK has a very low affinity for this guanosine analog. The toxicity of ganciclovir is manifested only when cells undergo DNA replication and it is not harmful to normal nondividing cells. This treatment strategy has been used for hepatocellular carcinoma (Huber, et al., 1991; Su, et al., 1996), fibrosarcoma, glioma (Culver, et al., 1992, see below), adenocarcinoma (Osaki, et al., 1994) and prostate cancer (Eastham, et al., 1996).

This patent proposes other suicidal genes instead of HSV-tk such as the cytosine deaminase (CD) gene. The CD protein catalyzes the conversion of the prodrug 5-fluorocytosine (5FC) to 5-fluorouracil (5FU); treatment of cells, transfected with this construct, with 5FC results in the conversion of the 5FC into the antitumor drug 5FU into CD-positive tumor cells (Mullen, et al., 1992; Austin and Huber, 1993; Huber, et al., 1993; 1994; Richards, et al., 1995).

This approach has been used for the treatment of primary and metastatic hepatic tumors based on the overexpression of the suicidal CD gene under control of the regulatory regions of the tumor marker gene carcinoembryonic antigen (Richards, et al., 1995, see below).

SUMMARY OF THE INVENTION

A method for the treatment of a variety of human malignancies is claimed which consists of the following components:

(i) A wild-type (wt) p53 cDNA expression vector, mutagenized at the Pax5-binding site, under control of the CMV, β-actin, or other promoters, and human origins of replication able to sustain long term expression of the p53 gene; viral origins of replication which require viral replication initiator proteins such as T antigen for their activation are nor suitable for the transfer of the p53 gene because p53 protein interacts strongly with T antigen (Lane and Crawford, 1979). U.S. patent application Ser. No. 08/884,025 filed Jun. 27, 1997, now U.S. Pat. No. 5,894,060 issued Apr. 13, 1999 shows how to isolate origins of replication directly from human genomic DNA.

A.(ii) A Pax5 cDNA expression vector, the only suppressor of the p53 gene known (both of the wt and mutant p53 genes) interacting with a short (10 nucleotide) regulatory region within exon 1 of the p53 gene (Stuart, et al., 1995). A major drawback in p53 gene therapy is the inactivation of the wt p53 protein by the endogenous mutated forms of p53 which are overexpressed in tumors and which are able to tetramerize with wt p53 protein; the endogenous p53 genes will be suppressed by expression of Pax5, a potent transcriptional repressor of the p53 gene. The wt p53 cDNA vector is mutagenized at the Pax5-binding site and by consequence the suppressive effect of Pax5 protein cannot take place. It is important to suppress the endogenous mutant p53 gene expression and eliminate mutant p53 from the cancer cells to potentiate induction of apoptosis and tumor suppression (iii) The herpes simplex virus thymidine kinase (HSV-tk) gene. The herpes simplex virus thymidine kinase (HSV-tk) suicide gene will be also included in combinations of p53 and Pax5 genes causing interruption in DNA synthesis after ganciclovir (GCV) treatment of the animal model and human patient; this is expected to increase the strand breaks in the cancer cells and to potentiate the tumor suppressor functions of p53 known to bind to strand breaks and to damaged DNA sites. Because of the combination of HSV-tk and p53 gene transfer, even expression of low therapeutic levels of the two proteins are expected to display and synergistic effect and potentiate tumor cell eradication for the reasons explained in this patent application.

Tumor cell mass in prostate cancer as well as in most other human cancers consists of an heterogeneous population of cells with respect to their ploidy, chromosomal translocations or deletions, and type of mutations in oncogenes and tumor suppressor genes. p53 tumor suppressor is mutated in over 70% of human cancers including prostate cancer; at early stages of carcinogenesis tumor cells may display mutations in one of the two p53 alleles and at both alleles at advanced stages. The endogenous mutated p53 interferes with the wild-type p53 (wt p53) function during gene transfer to cancer cells and it might be hard to achieve satisfactory expression levels and therapeutic effects with wild-type p53.

RATIONALE OF THE INVENTION

Gene therapy is a new era of biomedical research aimed at introducing therapeutic genes into somatic cells of patients (reviewed by Anderson, 1992). Two major obstacles prohibit successful application of somatic gene transfer: (1) the small percentage of transduced cells and (2) the loss of the transcription signal of the therapeutic gene after about 3–7 days from injection in vivo (reviewed by Boulikas, 1996a–e).

The first problem arises (i) from inability of delivery vehicles carrying the gene to reach the target cell surface (the vast majority of liposome-DNA complexes are eliminated from blood circulation rapidly); (ii) from difficulty to penetrate the cell membrane and (iii) to release the DNA from endosomes after internalization by cells; (iv) from inefficient import into nuclei. Our aim is to use stealth-cationic liposomes, which persist in circulation for days and concentrate in tumors. However, stealth liposomes are not taken up by cancer cells. Strategies are designed to enhance liposome internalization (PEG fall-off).

The second problem results from the loss of the plasmids in the nucleus by nuclease degradation and failure to replicate autonomously leading to their dilution during cell proliferation among progeny cells or by inactivation of the foreign DNA after integration into the chromosomes of the host cell. Our aim is to use human sequences able to sustain extrachromosomal replication of plasmids for prolonged periods. Viral origins of replication requiring T antigen or another viral initiator protein for their activation (Thierry, et al., 1995; Gassmann, et al., 1995) cannot be used for p53 delivery because of the strong binding of p53 to these proteins.

Transfer of the wild-type p53 gene has been successfully used to slow-down tumor cell proliferation in vivo and in cell culture in numerous studies (Diller, et al., 1990; Isaacs, et al., 1991; Chen, et al., 1991; Wills, et al., 1994; Fujiwara, et al. 1994) and intratumoral injection using adenoviral/p53 vectors has been shown to be effective against lung tumors in recent clinical trials (Roth, et al., 1996) and against prostate tumors on animal models (Ko, et al., 1996). The intratumoral injection method, however, may not be applicable to metastases often associated with late stages of cancer. Systemic delivery of the p53 gene and targeting of tumors in any region of the body might be a drastic treatment for cancer and its metastases. We claim strategies ameliorating four of the steps for somatic gene transfer using liposomal delivery of the wt p53 gene into a variety of human cancers in animal models and in patients to be tested in Clinical trials. These include: (i) concentration of the gene bullets into solid tumors, (ii) enhancement in uptake of p53/Pax5/HSV-tk plasmids by cancer cells, (iii) sustained expression of the genes using human origins of replication (ORIs) able to sustain episomal replication of plasmids for long periods in nuclei resulted in sustained expression of the transgenes, and (iv) potentiation of the p53 tumor suppressor activity by the Pax5 strategy, as well as in combination with HSV-tk and GCV.

We claim tumor regression and reduction in tumor mass volume of prostate and other cancers in animal models and in humans after delivery of a combination of the p53, Pax5, and HSV-tk genes using modified Stealth® liposomes followed by ganciclovir treatment.

Several experimental strategies for cancer treatment have been designed using p53 gene delivery; our novelty consists in that the endogenous mutant p53 forms, which are overexpressed in over half of human prostate malignancies (Isaacs, et al., 1991) especially those from advanced prostate cancer (Chi, et al., 1994; Dinjens, et al., 1994; reviewed by Boulikas, 1996e), are suppressed using the Pax5 expression vector (Stuart, et al., 1995). Mutated forms of p53 have amino acid substitutions mainly in their DNA binding domain but are still able to tetramerize with the wt p53 form; p53 acts as a tetramer and the presence of high levels of endogenous mutant p53 in human cancers cells interferes with the tumor suppressor functions of the wt p53 to be delivered.

Pax5 is an homeodomain protein which determines body structures during development; Pax5 is expressed at early stages of mammalian development and in the adult during differentiation in hematopoietic stem cells; p53 gene expression is eliminated by the Pax5 suppressor protein at early stages of development allowing cells to multiply fast in the developing embryo. Pax5 is switched off at later stages throughout adulthood allowing p53 to be expressed and exert its tumor suppressive functions and to regulate apoptosis especially in the hematopoietic cell lineage (Stuart, et al., 1995).

DETAILED DESCRIPTION OF THE INVENTION

We claim treatment of rat models of prostate cancer, mouse models of colon, breast and head and neck squamous cell carcinomas, and more important of a variety of human cancer patients by introduction of a combination of p53/Pax5/HSV-tk genes into the tumor cells. Our approach consists of two major parts: (i) the ability to target cancer cells (ii) effectiveness of our approach to kill cancer cells. A number of delivery systems are being used in somatic gene transfer, each associated with advantages and drawbacks. Recombinant adenoviruses do not replicate efficiently; recombinant murine retroviruses integrate randomly and are inactivated by chromatin surroundings; AAV integrates at chromosome 19 but needs helper adenovirus for infection. All have a maximum capacity of 3.5–7.5 kb of foreign DNA because of packaging limitations. Naked DNA is rapidly degraded (half-life 5 minutes) after systemic delivery (Lew, et al., 1995). Cationic liposomes do not survive in circulation beyond a heart beat and target mainly the endothelium of the lung, liver, and heart. So far, only Stealth® liposomes have been proven capable of concentrating in tumor sites (also in liver and spleen) and to survive for prolonged periods in blood circulation (e.g., one day compared with minutes for non-stealth neutral liposomes and a few seconds for cationic liposomes). However, stealth liposomes are not taken readily by tumor cells remaining in the extracellular space where they release their load over days after lysis; we propose to modify stealth liposomes with PEG which falls off (in collaboration with SEQUUS) exposing a partially neutral-partially cationic liposomal surface which would then enter the cell by poration or via caveolae avoiding degradation of the genes they engulf into lysosomes. Condensation of the DNA with histone H1, total histones, and HMGs will increase the nuclear import of the plasmid.

Having attained concentration and uptake of the gene bullets in solid tumors in animals with stealth liposomes, the second step is efficacy of our gene targeting approach. A number of studies support the idea that expression of the wt p53 gene in cancer cells in culture as well as in animals and clinical trials in vivo is of the most efficient means to kill cancer cells (Diller, et al., 1990; Chen, et al., 1991; Isaacs, et al., 1991; Bacchetti and Graham, 1993; Wills, et al., 1994; Fujiwara, et al., 1994). A human clinical trial at M. D. Anderson Cancer Center uses transfer of the wild-type p53 gene in patients suffering with non-small cell lung cancer and shown to have p53 mutations in their tumors using local injection of an Ad5/CMV/p53 recombinant adenovirus at the site of tumor in combination with cisplatin (Roth, 1996). The first results of this clinical trial are encouraging after intratumor injection of p53 (Roth, et al., 1996). However, local injection is not applicable to metastases often associated with advanced stages of malignancies; in particular, prostate cancer gives metastases to bones by a mechanism involving stimulation in prostate tumor proliferation by insulin-like growth factor I (IGF-I) which is especially secreted by bone cells. Therefore, the delivery system proposed here, able to concentrate into the tumor cell mass after systemic injection, is likely to treat not only the primary tumor but also its metastases.

The claims in this patent provide a potent gene therapy strategy applicable against a variety of human malignancies. The strategy is based on the suppression of the endogenous mutant p53 gene in cancer cells by the Pax5 expression vector; Pax5 expression will not affect the wt p53 gene expression because it lacks the Pax5 binding site located in the first exon of the p53 gene (Stuart, et al., 1995). Furthermore, the same strategy uses the herpes simplex virus thymidine kinase gene and treatment with the guanine analog ganciclovir expected to create strand breaks and disruption in DNA replication by arresting the replication forks; the incurred strand breaks are expected to bind wt p53 also expressed in the same type of cells thus potentiating the tumor suppressor function of p53 and the induction of the death pathway because of the accumulated damage on DNA.

Part of the claims are based on the ability to encapsulate plasmid DNA into Stealth® liposomes and the demonstrated concentration of this type of liposomes into tumors (SEQUUS patent). One major claim is to place all three genes (p53, Pax5, HSV-tk) under control of tumor-specific elements, such as the regulatory regions of the carcinoembryonic antigen (CEA), the BRCA1, the prostate-specific antigen (PSA), and other genes depending on the targeted tumor cell type.

Although by the year 2002–2003 the human genome project is expected to be completed we will be lacking information on the location of an estimated minimum of 450,000 regulatory regions; these include two enhancers or more and one promoter for each one of the 125,000 genes, plus about 50,000 ORIs, -one for every chromatin loop-, and an undetermined number of locus control regions, silencers, and boundary elements or MARs. A detailed understanding of the nature of regulatory regions in the postgenomic era and development of novel technologies for their isolation from nuclei of specific cell types would permit to pinpoint the regulatory regions among the $3\times10^9$ bp of human sequences. Relevant to this are efforts from our laboratory and other laboratories that culminated with the isolation of regulatory sequences from the human genome based on the MAR technology (Boulikas, et al., 1997). Such sequences will be used to increase the time of expression of p53 in animal tissues.

One of the strengths of this patent is that it uses human ORIs for the episomal replication of the genes. Episomal vectors using viral ORIs and T antigen to activate the viral ORI (e.g., Thierry, et al., 1995; Gassmann, et al., 1995) cannot be applied for the expression of p53 because p53 interacts with T antigen (Lane and Crawford, 1979; Linzer and Levine, 1979). Also, adenoviral vectors expressing E1B are not appropriate for the delivery of wt p53 because of the formation of an E1B-p53 complex leading to p53 inactivation (van den Heuvel, et al., 1990). Oncogenic viruses are believed to cause cancer by interaction of p53 with viral proteins, leading to p53 inactivation from inability to exert its tumor suppressive functions. Retroviruses are suitable for p53 delivery and have entered clinical trials (Roth, et al., 1996). However, retroviruses integrate randomly into the host genome and are inactivated by chromatin surroundings.

Transfer of the wt p53 along with Pax5 cDNA expression is expected to be more effective than transfer and expression of the wt p53 gene alone rendering the tumor cells amenable to apoptosis or programmed cell death.

Specific expression of the wt p53 in prostate cancer cell and its bone and other tissue metastases is effected using the promoter/enhancer/matrix-attached regions (MARs) of the prostate-specific antigen (PSA), a protein expressed specifically in prostate tumor but not in normal prostate cells; PSA is detected in the serum in humans in screening tests and is a powerful diagnostic tool for early as well as advanced stage of the disease. MARs are identified using the cloned gene fragments from the PSA gene and nuclear matrices, containing the minimal amount of MAR DNA in an in vitro MAR-binding assay.

We expect to determine the type of control elements among CMV, RSV, b-actin promoter, CHAT ORI, and SV40 promoter which is best to drive the p53 gene for each type of cancer in the animal model. We expect to find differences between different regulatory elements for each type of cancer because of relative differences in transcription factor levels required for the activation of these sequences among cell types (prostate, colon, HNSCC) (reviewed by Boulikas, 1994).

The proposed approach will only target dividing cells because of the use of HSV-tk and ganciclovir, and primarily vascularizing tumors because of the use of stealth liposomes. Thus, liver and spleen cells that are also reached by stealth liposomes will not be killed.

A. p53 versus P53 and Pax5

We claim that a combination of p53 with Pax5 is more efficient in killing cancer cells resulting in a more rapid shrinkage or eradication of the solid tumor than p53 vector alone. We expect that wt p53 expression will not be affected by expression of Pax5; this is because Pax5 protein is expected to suppress the endogenous mutated p53 gene in the tumor cells. These items will be tested by measuring quantitatively the wt p53 expressed in the tumor after p53 or p53 and Pax5 treatment of the animal. Similar studies will be done after transfection with HSV-tk in vivo. The GCV treatment is not toxic to the animal except for dividing cells transduced with HSV-tk (Culver, et al., 1992).

B. Preferential Expression of Suicidal Genes in Cancer Cells Using Promoters/Enhancers from Tumor-Specific Genes A number of tumor-specific control regions are claimed to drive the expression of p53/Pax5/HSV-tk genes in tumor cells. Studies by others have shown targeting of hepatocellular carcinoma using the regulatory region from the tumor-specific a-fetoprotein gene to drive the Varicella zoster thymidine kinases gene (Huber, et al., 1991); treatment of primary and metastatic hepatic tumors based on the overexpression of the suicidal gene cytosine deaminase (CD) from E. coli under control of the regulatory regions of the tumor marker gene carcinoembryonic antigen (CEA) (Richards, et al., 1995). Regulatory sequences from the CEA gene (−322 to +111 bp) were also used to express the HSV thymidine kinase gene in pancreatic and lung neoplasms (Dimaio, et al., 1994; Osaki, et al., 1994).

It is claimed that this approach is applicable to target specific types of tumors.

The following example is intended to illustrate but in no way to limit the invention.

Materials and Methods

A. Construction of Expression Vectors

We have constructed efficient episomal vectors where the gene is under influence of the cytomegalovirus (CMV) immediately early (IE) promoter, Rous sarcoma virus (RSV) promoter, and MARs from the human CHAT gene (Boulikas, et al., 1997a,b; Boulikas and Hu, 1997) able to sustain about 100 to 1000-fold higher levels of expression of the luciferase reporter gene in vivo compared with commercially available expression vectors (e.g., pGL3-C of Promega Biotech, Madison, Wis.; pMAMneoLuc of Clonetech, Palo Alto, Calif.); These vectors include pLF, pdLF, pdLFd, pLFZ, and $pL_{rsv}F$. The expression of the luciferase from pdLFd persists after cell culture transfection for more than 4 months, which is of the highest to be yet reported.

The plasmid is replicated in human cells as an episomal element (Boulikas, et al., 1997a).

A new plasmid is constructed containing: (i) the p53 gene under control of the cytomegalovirus immediately early (CMV IE) promoter and a strong ORI from the human genome arising from the ORI trap method; (ii) the Pax5 gene under control of the CMV IE promoter and the same ORI so as Pax5 will be subjected to the same regulatory constrains with p53 in nuclei of transfected tumor cells; (iii) the HSV-tk gene under control of the same elements.

Since only a small percentage of cells may be targeted resulting in the ultimate nuclear import of only a single plasmid from a mixture of three, engineering a larger plasmid containing all three genes together is a great advantage.

It is claimed that in order to measure the expression of the various transgenes in cell culture and in animal tissues and in the tumor of the animal, the DU145 cell line is used that has been shown to have a mutated form of p53 (Isaacs, et al., 1991). The Dunning rat model of human prostate cancer is used; rats are injected intravenously using the tail vein with 100 mg of the mixture of the three plasmids in equimolar amounts or the plasmid with all three genes after its condensation and encapsulation into stealth-cationic liposomes. p53 will be detected with commercially available antibodies.

It is claimed that the optimal conditions leading to regression of prostate tumors in rats and a variety of tumors in humans need to be determined in order to validate the therapeutic value of this approach. For example, control experiments using only two plasmid pairs (p53+Pax5 or p53+HSV-tk) and experiments where the relative stoichiometric amounts of the three plasmids are modified are expected to define the most effective conditions for cancer therapy.

In order to detect p53, Pax5, and HSV-tk in the tissues of the animal including the solid tumor the genes are constructed as fusion proteins with green fluorescent protein from the vector pGFP-N1 of Clontech. The proteins are detected under the fluorescence microscope by direct visualization of the cancer tissue.

Because the p53/GFP fusion protein might interfere with the tumor suppressor/apoptosis functions of p53, different constructs are made containing small peptides of about 7–10 amino acids as fusion products with the N- or C-terminus of p53. These peptides represent epitopes in proteins for which antibodies are available for their detection.

The genes are excised from commercially available plasmids or donations from laboratories: p53 and HSV-tk are from American Type Culture Collection (ATCC), Pax5 from Peter Gruss, Germany. Genes are placed under control of the CMV IE control element as described for construction of plasmid pLF (Boulikas, et al., 1997a). Control plasmids (pLF) containing the luciferase reporter gene are also used as well as inserts of the genes into the pLF plasmid; luciferase assays will reveal the distribution of expression in animal tissues.

B. Use of Human ORIs to Sustain Expression of Transgenes

Three key steps appear to be involved in effective gene transfer to somatic cells or to cells in culture: (i) vehicle for delivery (liposomal, adenoviral, retroviral, etc.) determining not only half-life in circulation, biodistribution in tissues, and efficacy of delivery but also the route through the cell membrane and fate in the nucleus; (ii) port of entrance to the cell, release of the DNA molecule from cytoplasmic compartments, and nuclear import; (iii) type and potency of regulatory elements for driving the expression of the transferred gene in a particular cell type including parameters that might determine integration versus maintenance of a plasmid or recombinant virus/retrovirus as an extrachromosomal element.

We propose strategies to test putative human origins of replication for their ability to sustain extrachromosomal replication of therapeutic plasmids for several weeks or months compared to a few days in current studies. We shall test initially the ability of the K19D fragment (513 bp) from the 3.6 kb clone isolated in our laboratory as the matrix-attached region and origin of replication of the human CHAT gene. This fragment has been inserted as one copy (pdLF) or two copies (pdLFd) in the pLF vector and has been shown to sustain episomal replication up to 4 months. In K562 cells in culture. Additional human sequences are available to be tested; these will be inserted into the plasmids carrying the p53, Pax5, and HSV-tk genes and the expression of p53 as well as tumor regression will be determined at time intervals, up to months, after systemic delivery of the plasmid with stealth-cationic liposomes.

C. Liposome Preparation

Liposomes can be prepared by various methods including reverse phase evaporation, dehydration-rehydration, detergent dialysis, and thin film hydration followed by sonication or extrusion through membranes of 400 down to 50-nm diameter pores. Liposomes are prepared either by ultrasonication or by sequential extrusion through 0.2, 0.1, and 0.05 mm membranes, 5 times each.

D. Plasmid Encapsulation

For plasmid encapsulation, spermine, histone-, or HMG-condensed supercoiled plasmid DNA are mixed with small unilamellar vesicles of average diameter of 60 nm obtained by ultrasonication; the mix will be frozen immediately using a dry ice/ethanol bath, lyophilized and hydrated. The degree of encapsulation will be controlled by 0.3% agarose gel electrophoresis able to determine the amount of free plasmid which is neither encapsulated nor complexed (Boulikas and Martin, 1996).

E. DLS Measurements

A Coulter N4M light (Coulter, Hialeah, Fla.) scattering instrument is used, at 90° angle, set at a run time of 200 sec, using 4 to 25 microsec sample time. The scan of the particle size distribution is obtained in 1 ml sample volume using plastic cuvettes, at 20° C. and at 0.01 poise viscosity.

F. Transfections and Luciferase Assays in Cell Culture

Prostate human cancer DU145 cells (from American Type Culture Collection) are cultured in RPMI 1640 medium supplemented with 9% fetal bovine serum, 0.1 mg/ml streptomycin, and 100 units/ml penicillin. Cell cultures are transfected by the direct addition of spermine-condensed DNA/liposome complexes in the presence of OPTI-MEM medium. The liposome formulation are DDAB:DOPE (1:1). At various times (1–7 days) posttransfection 0.5 ml cell culture (about 250,000 cells) is withdrawn into Eppendorf tubes, spun in a microfuge for 30 seconds, washed once in PBS, and the cell pellet is lysed directly into 0.5 ml luciferase lysis buffer (1% Triton X-100, 1 mM dithiothreitol, 2 mM EDTA, 100 mM Tris pH 8.0, 1 mM phenylmethylsulphonyl fluoride) and centrifuged for 2 minutes in Eppendorf tubes (13,000 g). 0.02 ml of the supernatant is assayed for luciferase activity using an automated luminometer, set at a 30 second reading time per well and a 3 second delay between wells and the Promega (Madison, Wis.) luciferase assay buffer kit. The samples are assayed for protein using the BioRad kit (BioRad, Richmond, Va.) and an automated 96-well reader of the colorimetric reactions. The luciferase values are normalized and expressed as relative luciferase units per mg protein.

G. Animal Injections and Luciferase/p53 Assays in Animal Tissues 0.3 mg plasmid is partially condensed in the presence of 0.03 mM spermine 0.15 mg total calf thymus histone at RT for 10 min in a total volume of 1 ml in the presence of 50 dextrose or 0.9% NaCl. The preparation is then complexed with 600 nmoles liposomes (DDAB:cholesterol 1:1) at RT for 1h.

Plasmids are encapsulated into Stealth® cationic liposomes DDAB:cholesterol:PEG-DSPE (10:10:1) with PEG-linked via S-S bonds to lipids (synthesized at SEQUUS Pharmaceuticals, Inc., Menlo Park, Calif.); these preparations are included in the place of PEG-DSPE for the preparation of Stealth®-cationic liposomes containing labile PEG chains.

The plasmid-spermine-liposome complex is divided into three equal parts and is injected (0.1 mg DNA per mouse; 0.4 mg per rat) to the tail vein of prostate cancer rat models or to the tail vein of Balb/c mice with established subcutaneous colon cancer tumors. At 2, 7, and 30 days postinjection, 3 animals per group will be anesthetized and perfused with buffer by cardiac effusion after cutting the portal vein to remove blood from tissues which interferes with luciferase assay. Two different methods will be used for luciferase assay in animal tissues. The solid tumor, lung, liver, spleen, and kidneys of the animal will be frozen in liquid nitrogen and ground to a fine powder; the ground tissue will be hydrated in buffers containing "TRITON" X-100 for cell lysis and will be processed similarly to the second method. According to the second method, the different organs will be homogenized in 0.5 ml phosphate-buffered saline (PBS) using a piston homogenizer for 1 min, will be incubated with collagenase to help dissolve the tissue; cells will be lysed by the addition of 0.2 ml of five times concentrated lysis buffer (see above) and transferred into Eppendorf tubes. Tissue cells will be further broken by three cycles of freeze-thawing using an ethanol-dry ice bath and a 37° C. water bath (10 min in each). Samples will be centrifuged at 13,000 g for 8 min and a 0.02 ml aliquot of the supernatant will be assayed for luciferase activity; another aliquot will be assayed for protein concentration as described above. p53 will also be determined using the monoclonal since p53 is under influence of the same control elements as luciferase/GFP, the convenient measurement of luciferase in animal tissues and in solid tumors will reveal the amount of expression of p53. This fact will be established and luciferase expression will be used as a diagnostic tool of p53 expression only; p53 expression will be determined independently of luciferase.

H. Treatment of Cancer Patients

Treatment of human cancer patients by intravenous infusion of 10 mg plasmid DNA encapsulated into liposomes is suggested until the toxicity and the efficacy of the dose are established on Clinical Trials This is about 30-fold lower than the doses used for laboratory animals. This simple fact necessitates the use of strong regulatory elements to demonstrate expression of therapeutic levels of the genes in human tumors.

I. Encapsulation of Mercaptoethylamine

Mercaptoethylamine is dissolved at 10 mg/ml in water to hydrate the dry film of stealth cationic lipids; the non-encapsulated drug is removed by dialysis against large volumes of 10 mM Tris pH 7.5. Stealth® liposomes loaded with mercaptoethylamine are injected to the same animals or human patients after the first infusion of the therapeutic plasmid in order to cause PEG hydrolysis. These are expected to be localized in the same tumor area releasing mercaptoethylamine and causing PEG to fall off from the surface of liposomes. The exposed DDAB cationic groups are expected to mediate membrane poration or uptake via caveolae.

J. Transduction of the Suicidal HSV Thymidine Kinase Gene Followed by Treatment with Ganciclovir A rather successful gene transfer approach results in the direct suppression of tumor growth by cytotoxic gene therapy. Cancer cells can be induced to be conditionally sensitive to the antiviral drug ganciclovir after their transduction with the thymidine kinase (tk) gene from the herpes simplex virus (HSV). This treatment strategy has been used for hepatocellular carcinoma (Huber, et al., 1991; Su, et al., 1996), fibrosarcoma, glioma (Culver, et al., 1992), adenocarcinoma (Osaki, et al., 1994) and prostate cancer (Eastham, et al., 1996).

Microinjection of HSV-tk gene, under control of alpha-fetoprotein enhancer and albumin promoter, in a linear form flanked by the adeno-associated virus inverted terminal repeats into pronuclei of mouse embryos led to transgenic animals expressing preferentially HSV-tk into adult liver cells; these transgenic animals were used for the treatment of hepatocellular carcinomas (Su, et al., 1996).

Retrovirus-mediated transfer of HSV-tk was used to kill proliferating cells in rabbit models of proliferative vitreoretinopathy (PVR); PVR may ensue after retinal surgery or trauma. Injection into the vitreous cavity of rabbit dermal fibroblasts transduced in vitro with retroviral vectors carrying the HSV-tk gene was used to preferentially kill proliferating cells for PVR in rabbit models; all eyes received 0.2 mg GCV on the following day and on day 4; significant inhibition of PVR was observed thus providing a novel therapeutic strategy for this disease (Kimura, et al., 1996).

Subcutaneous tumors induced by injection of RM-1 (mouse prostate cancer) cells in mice followed by injection of HSV-tk in an adenovirus vector and treatment with ganciclovir for 6 days showed reduction in tumor volume (16% of control) and higher apoptotic index in tumor cells (Eastham, et al., 1996).

The bystander effect of the HSV-tk plus GCV system appears to be powerful and significant, circumventing the low efficiency of transduction in vivo with recombinant retroviruses. The low-level percentage of cells that can be transduced with a retrovirus can cause the elimination of a much larger percentage of proliferating cells in their surroundings (Kimura, et al., 1996).

We shall transfer the HSV-tk gene to solid tumors in animal models using liposomes in combination with p53, and Pax5, or alone (as a control). The regression in the volume of the tumor after GCV treatment will be measured. Also the expression of HSV-tk will be determined at 2, 7, and 30 days from delivery in the solid tumors and other organs using mRNA isolation from the tissue, reverse transcription to cDNA using the Clontech kit and PCR with primers specific for the viral gene.

K. Treatment with Ganciclovir (GCV)

Ganciclovir is the 9-{[2-hydroxy-1-(hydroxymethyl)-ethoxy]methyl}guanine (Field, et al., 1983); it is converted by HSV-tk into its monophosphate form which is then converted into its triphosphate form by cellular enzymes and is then incorporated into the DNA of replicating mammalian cells leading to inhibition in DNA replication and cell death (Moolten, 1986; Borrelli, et al., 1988; Moolten and Wells, 1990). It is only viral TK, not the mammalian enzyme, that can use efficiently ganciclovir as a substrate and this drug has been synthesized to selectively inhibit herpes virus replication (Field, et al., 1983); indeed, the mammalian TK has a very low affinity for this guanosine analog. The toxicity of ganciclovir is manifested only when cells undergo DNA replication and it is not harmful to normal nondividing cells. Systemic treatment of the animals with ganciclovir will be performed as described elsewhere (Huber, et al., 1991; Eastham, et al., 1996) using two IV injections per week using 0.05 mg/g body weight of the animal.

L. DpnI Assays on Hirt Extracts

Any cloned fragment of DNA can be tested for its efficacy to drive the autonomous replication of a bacterial plasmid after its introduction into cells in culture in transient transfection experiments. The method of preference for testing replication of a DNA fragment in higher eukaryotes is the DpnI-resistance assay on Hirt extracts (Hirt, 1967) at 48–72 post-transfection. According to this method, cells are lysed with SDS in the presence of about 0.5 M NaCl; the lysate is left at 0° C. for several hours. Under these conditions high molecular weight genomic DNA forms a large complex with the SDS-NaCl complex which can be removed following centrifugation at 13,000 to 25,000 g for about 30 min-1 h leaving the low size plasmid or viral DNA in the supernatant (Hirt, 1967). The plasmid DNA in the supernatant is extracted, digested with DpnI, the fragments are separated by electrophoresis on agarose gels, and blotted on nylon or nitrocellulose filters using the bacterial plasmid as a probe. DpnI-resistant plasmids are those replicated in eukaryotic cells and lacking methylation on adenine residues characteristic of molecules replicated in *E. coli*. It is only bacterially-made DNA that carries methylated A that is cleaved by DpnI.

However, identification of a genomic sequence that confers autonomous replication to a plasmid does not imply that the sequence functions as an origin of replication in vivo. In fact, only a fraction of yeast sequences that drive the autonomous replication of plasmids map to chromosomal origins of replication (Dubey, et al., 1991). It is believed, however, that most sequences capable of driving the extrachromosomal replication have sequence motifs characteristic of ORIs and could potentially be used as origins at a certain developmental stage or cell type.

At 72 h post-transfection the cells will be lysed and low molecular weight DNA will be isolated according to Hirt (1967). Hirt extracts will be linearized with BamHI or EcoRI and then digested with DpnI. This restriction enzyme cleaves fully methylated DNA (such as DNA grown in adenine methylase-positive HB101 *E. coli*) at the sequence G$^m$ATC, but it is unable to cleave the GATC recognition site when the A residue is not methylated (i.e. when the DNA is replicated in mammalian cells). Linearized and DpnI-digested DNA fragments will be separated by electrophoresis on agarose gels, transferred to nitrocellulose or nylon membranes and hybridized using pBS as a probe. For this purpose, pBS will be labeled with a [$^{32}$P] ATP using the nick translation method of Amersham. The intensity of the DpnI-resistant band from each of the MAR/pBS plasmids will be compared to that of pBS alone.

M. DNA Sequencing

DNA sequencing is performed using an automated DNA sequencer (ALF system, Pharmacia, Piscataway, N.J.). All plasmid constructs are verified by sequencing.

N. p53 Expression

The level of expression of p53 is determined using monoclonal antibodies against p53 on filter membranes after transfer of the proteins extracted form rat prostate tumors on polyacrylamide gels. Western blot analysis is performed using the DO-1 no. SC-126 monoclonal antibody (Santa Cruz Biotechnology, Santa Cruz, Calif.) at 100-fold dilution (Westerman and Leboulch, 1996).

Additional Claims Overlapping with Other Patents

I. Delivery of the P53/Pax5/HSV-tk Genes to Solid Tumors with Modified Stealth Liposomes We propose to target prostate and other cancer cells in animal models and humans using transfer of the wild-type (wt) p53 gene in combination with Pax5 and HSV-tk. p53 has been shown to be mutated and overexpressed in more than 50% of human malignancies; delivery of the wt-p53 gene to tumor cells has been shown to be a very effective treatment against cancer by inducing apoptosis or arrest in the cell cycle. However, the application of the method in vivo is inadequate, mainly due to failure of plasmids, retroviruses, or liposomes carrying the p53 gene to target preferentially solid tumors after systemic injection. Stealth® liposomes (coated with polyethyleneglycol, PEG) are known to extravasate through new blood vessels formed during angiogenesis and to concentrate in solid human tumors; however, they are not taken up by the cells. Cationic liposomes are cleared from blood circulation in 1 sec. (one heart beat) taken rapidly by endothelial cells. It is proposed here to use p53/Pax5/HSV-tk vectors encapsulated into stealth-cationic liposomes coated with PEG which is attached to lipids via disulfide bonds and a PEG fall-off strategy exposing cationic lipids on the surface of the liposomes, after concentration in tumors, to enhance uptake by poration of the cell membrane.

It is claimed:

1. A vector combination for use in cancer treatment, comprising (a) a wildtype (wt) p53 expression vector containing (i) a promoter active in tumor cells, (ii) a human p53 gene under the control of said promoter, said gene being mutagenized at its Pax5-binding site to inhibit or prevent gene suppression by Pax5 protein, and (iii) a human origin of replication able to sustain long term expression of the p53 gene in tumor cells; and (b) a Pax5 expression vector containing (i) a promoter active in tumor cells, (ii) a human Pax5 gene under the control of said promoter, and (iii) a human origin of replication able to sustain long term expression of the Pax5 gene in tumor cells.

2. The combination of claim 1, which further includes a herpes simplex virus thymidine kinase (HSV-tk) expression vector containing (i) a promoter active in tumor cells, (ii) an HSV-tk gene under the control of said promoter, and (iii) a human origin of replication able to sustain long term expression of the HSV-tk gene in tumor cells.

3. The combination of claim 1, wherein the promoter in said vectors is selected from one of the group consisting of the cytomegalovirus immediately early (CMV-IE) promoter, the Rous Sarcoma virus (RSV) promoter, B-actin promoter, and SV40 promoter.

4. The combination of claim 1, wherein the vectors are packaged in liposomes coated with polyethyleneglycol (PEG) chains, where the liposomes have a cationic surface charge.

* * * * *